(12) United States Patent     (10) Patent No.:   US 12,685,840 B2

Burrough     (45) Date of Patent:     Jul. 21, 2026

(54) USER WORN GASTRONOMY TUBE RETAINING DEVICE AND METHOD OF USE

(71) Applicant: Donna Burrough, San Marcos, TX (US)

(72) Inventor: Donna Burrough, San Marcos, TX (US)

( * ) Notice: Subject to any disclaimer, the term of this patent is extended or adjusted under 35 U.S.C. 154(b) by 630 days.

(21) Appl. No.: 18/131,631

(22) Filed: Apr. 6, 2023

(65) Prior Publication Data

US 2024/0334989 A1     Oct. 10, 2024

(51) Int. Cl.
| | |
|---|---|
| *A61M 25/02* | (2006.01) |
| *A41D 13/12* | (2006.01) |
| *A61M 25/00* | (2006.01) |
| *A41B 9/00* | (2006.01) |

(52) U.S. Cl.
CPC ......... *A61M 25/02* (2013.01); *A41D 13/1254* (2013.01); *A61M 25/002* (2013.01); *A41B 9/008* (2013.01); *A61M 2025/0206* (2013.01); *A61M 2025/026* (2013.01)

(58) Field of Classification Search
CPC .... A61M 25/02; A61M 25/002; A61M 35/10; A61M 2025/0206; A61M 2025/026; A61M 3/027; A61J 15/0026; A61J 15/0053; A61J 15/0061; A41B 9/008; A41D 13/1254; A41D 13/1236; A41D 13/1245; A41D 2400/48; A41F 9/00; A41F 9/002; A61F 5/44; A61F 5/00; A61F 5/028; A61F 5/05
See application file for complete search history.

(56) References Cited

U.S. PATENT DOCUMENTS

| | | | | |
|---|---|---|---|---|
| 4,799,923 A | * | 1/1989 | Campbell ............. | A61M 25/02 604/179 |
| 4,898,587 A | * | 2/1990 | Mera ..................... | A61M 25/02 604/174 |
| 5,082,111 A | * | 1/1992 | Corbitt, Jr. ........... | A61M 25/02 206/478 |
| 5,188,586 A | * | 2/1993 | Castel ................ | A41D 13/0525 128/845 |
| 5,205,832 A | * | 4/1993 | Tuman .............. | A61M 16/0488 604/179 |
| 5,244,464 A | * | 9/1993 | Madden ................ | A61M 25/02 604/179 |
| 5,257,419 A | * | 11/1993 | Alexander ............. | A61F 5/028 2/338 |

(Continued)

FOREIGN PATENT DOCUMENTS

| | | |
|---|---|---|
| CN | 206167411 | 5/2017 |

*Primary Examiner* — William H Rodriguez

(57)       ABSTRACT

A user worn gastronomy tube retaining device for reducing inadvertent pulling of a gastronomy tube includes a first panel, which is resiliently flexible and removably securable around an abdomen of a user so that the first panel encircles the abdomen with an inner surface of the first panel in contact with the abdomen. A plurality of connectors is attached to an outer surface of the first panel, with each connector being selectively connectable to a gastronomy tube so that the gastronomy tube is attached to the first panel. The connector thus retains the gastronomy tube in a substantially static position relative to the abdomen and resists a pulling force that might be inadvertently applied to the gastronomy tube.

8 Claims, 7 Drawing Sheets

(56)         References Cited

U.S. PATENT DOCUMENTS

| | | | | | |
|---|---|---|---|---|---|
| 5,304,145 | A | * | 4/1994 | Blair | A61M 25/02 |
| | | | | | 604/179 |
| 5,381,801 | A | * | 1/1995 | McShane | A61F 5/56 |
| | | | | | 2/315 |
| 5,496,282 | A | * | 3/1996 | Militzer | A61M 25/02 |
| | | | | | 604/179 |
| 5,551,085 | A | * | 9/1996 | Leighton | A61F 5/028 |
| | | | | | 602/19 |
| 5,672,159 | A | * | 9/1997 | Warrick | A61M 16/0683 |
| | | | | | 604/179 |
| 5,765,224 | A | * | 6/1998 | Johnson | A41C 1/02 |
| | | | | | 2/45 |
| 6,270,485 | B1 | * | 8/2001 | Ekey | A61F 5/4408 |
| | | | | | 224/663 |
| 6,296,164 | B1 | * | 10/2001 | Russo | A61M 25/02 |
| | | | | | 224/660 |
| 6,419,652 | B1 | * | 7/2002 | Slautterback | A61F 5/028 |
| | | | | | 2/311 |
| 6,578,576 | B1 | * | 6/2003 | Taormina | A61M 25/02 |
| | | | | | 128/207.14 |
| 6,814,716 | B2 | | 11/2004 | Bouphavichith | |
| D503,478 | S | | 3/2005 | Kaushal | |
| 7,276,048 | B2 | | 10/2007 | Enroth | |
| 7,364,558 | B2 | * | 4/2008 | Weaver, II | A61F 5/028 |
| | | | | | 602/19 |
| 7,661,152 | B2 | | 2/2010 | Manzano-Rivera | |
| 8,292,860 | B1 | * | 10/2012 | Persichetti | A45F 3/14 |
| | | | | | 604/355 |
| 9,327,099 | B2 | * | 5/2016 | Wainscott | A61M 25/02 |
| D794,809 | S | * | 8/2017 | Gramza | D24/190 |
| 10,022,258 | B2 | * | 7/2018 | Arsenault | A61F 5/028 |
| 10,034,995 | B2 | * | 7/2018 | Kooij | F16L 3/13 |
| 10,207,079 | B2 | * | 2/2019 | Fee | A61M 25/02 |
| 10,765,908 | B1 | * | 9/2020 | Uehara | A63B 21/4001 |
| D939,310 | S | | 12/2021 | Zhang | |
| 11,583,657 | B2 | * | 2/2023 | Berg | A61M 25/0017 |
| 12,036,374 | B2 | * | 7/2024 | Jansson | A61M 5/1418 |
| 12,427,278 | B1 | * | 9/2025 | LaCorte | A61M 16/0875 |
| 2002/0029406 | A1 | * | 3/2002 | Meyer | A61M 25/02 |
| | | | | | 2/310 |
| 2003/0065289 | A1 | | 4/2003 | Clayton | |
| 2005/0059935 | A1 | * | 3/2005 | Yamazaki | A61M 1/3661 |
| | | | | | 604/179 |
| 2005/0070582 | A1 | | 3/2005 | Li | |
| 2009/0216197 | A1 | * | 8/2009 | Russo | A61M 25/02 |
| | | | | | 604/179 |
| 2010/0137805 | A1 | * | 6/2010 | Farchione | A61M 25/02 |
| | | | | | 604/179 |
| 2011/0023208 | A1 | * | 2/2011 | Liao | A61M 25/02 |
| | | | | | 2/102 |
| 2014/0298566 | A1 | * | 10/2014 | Rogers | A61M 35/10 |
| | | | | | 2/171.2 |
| 2014/0358090 | A1 | * | 12/2014 | Wainscott | A61M 25/02 |
| | | | | | 604/179 |
| 2016/0025630 | A1 | | 1/2016 | Jensen et al. | |
| 2016/0050995 | A1 | * | 2/2016 | Bentley | A41D 27/207 |
| | | | | | 2/114 |
| 2016/0158473 | A1 | * | 6/2016 | Schuster | A61M 16/0875 |
| | | | | | 128/207.14 |
| 2016/0213878 | A1 | * | 7/2016 | Browning, Jr. | A61M 16/0875 |
| 2016/0213886 | A1 | * | 7/2016 | DiGiorgi | A61M 25/02 |
| 2017/0014255 | A1 | * | 1/2017 | Booker | A61H 9/0078 |
| 2018/0207416 | A1 | * | 7/2018 | Roddy | A61M 39/24 |
| 2019/0134362 | A1 | * | 5/2019 | Fee | A61M 25/02 |
| 2020/0046047 | A1 | * | 2/2020 | Bentley | A41D 27/201 |

* cited by examiner providing a gastronomy tube — 50 providing a user worn gastronomy tube retaining device — 52 securing the first panel around an abdomen of the user — 54 connecting the gastronomy tube to the first panel using a respective connector — 56

48

USER WORN GASTRONOMY TUBE RETAINING DEVICE AND METHOD OF USE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to tube retainers and more particularly pertains to a new tube retainer for reducing inadvertent pulling of a gastronomy tube. The present invention discloses a tube retainer that is comfortably attachable to a user and to a gastronomy tube to prevent inadvertent pulling on the gastronomy tube.

(2) Description of Related Art Including Information Disclosed Under 37 CFR 1.97 and 1.98

The prior art relates to tube retainers, which may comprise lanyards, bands with pockets for receiving ends of tubes, wherein the bands are positionable around abdomens of users, belts with compartments attached, wherein the compartments contain tubes that can be extended through slots in backs of the compartments into stomata, and clips that are adhesively attachable to skin of abdomen. Related prior art includes belts having access panels that can be secured over stoma sites and head mountable tube retainers. What is lacking in the prior art is a tube retainer comprising a resiliently flexible panel that can be removably secured around an abdomen of a user and to which a plurality of connectors, with ach connector being selectively connect to a gastronomy tube.

BRIEF SUMMARY OF THE INVENTION

An embodiment of the disclosure meets the needs presented above by generally comprising a first panel, which is resiliently flexible and which is configured to be removably secured around an abdomen of a user so that the first panel encircles the abdomen with an inner surface of the first panel in contact with the abdomen. A plurality of connectors is attached to an outer surface of the first panel. Each connector is configured to selectively connect to a gastronomy tube so that the gastronomy tube is attached to the first panel. The connector thus is configured to retain the gastronomy tube in a substantially static position relative to the abdomen and to resist a pulling force that might be inadvertently applied to the gastronomy tube.

An embodiment of the disclosure includes a method of securing a gastronomy tube to a user. Provision steps of the method entail providing a gastronomy tube and a user worn gastronomy tube retaining device, according to the disclosure above. Operational steps of the method are securing the first panel around an abdomen of the user and connecting the gastronomy tube to the first panel using a respective connector.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
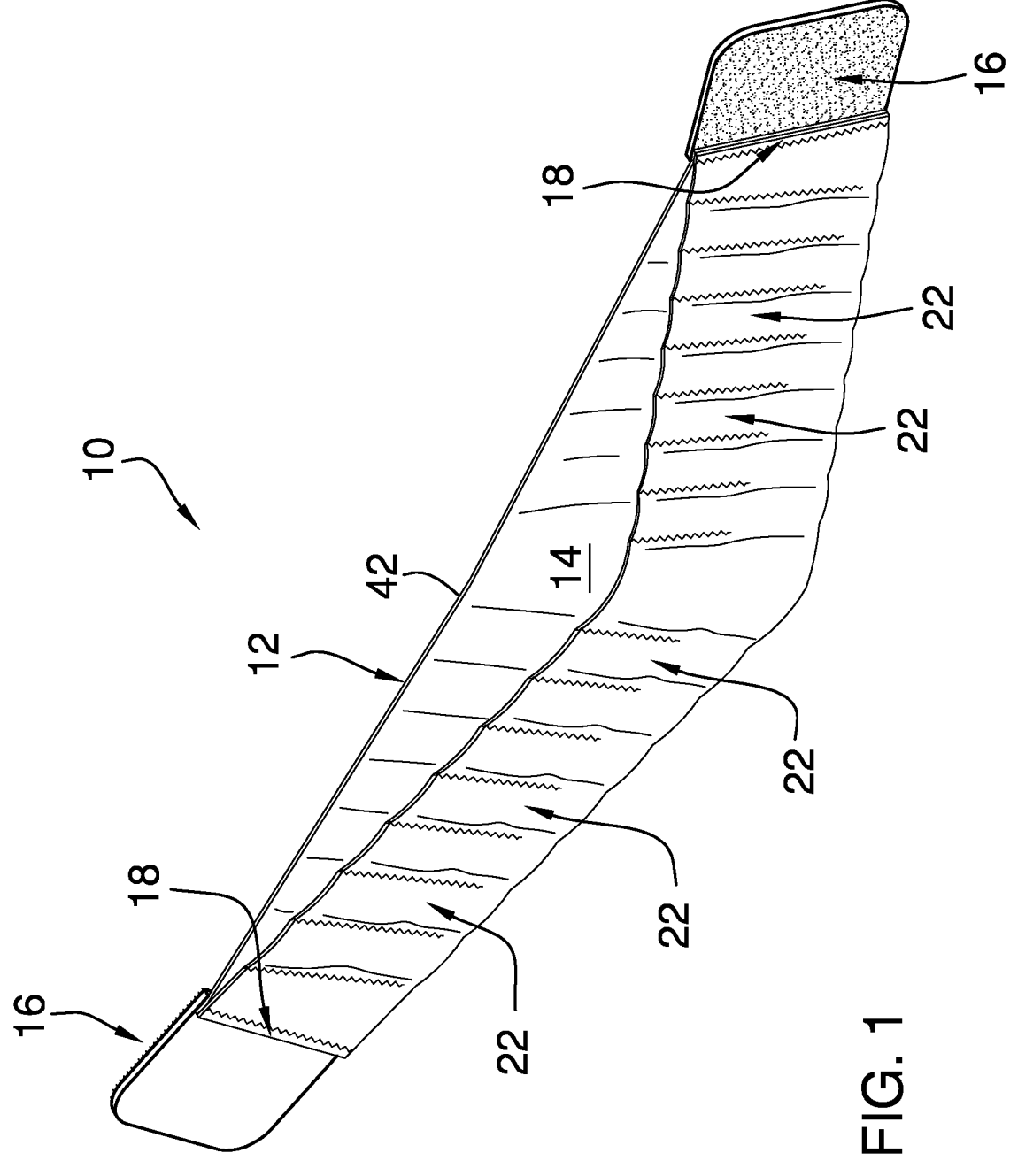
FIG. 1 is an isometric perspective view of a user worn gastronomy tube retaining device according to an embodiment of the disclosure.

With reference now to the drawings, and in particular to FIGS. 1 through 8 thereof, a new tube retainer embodying the principles and concepts of an embodiment of the disclosure and generally designated by the reference numeral 10 will be described.

Figure 2:
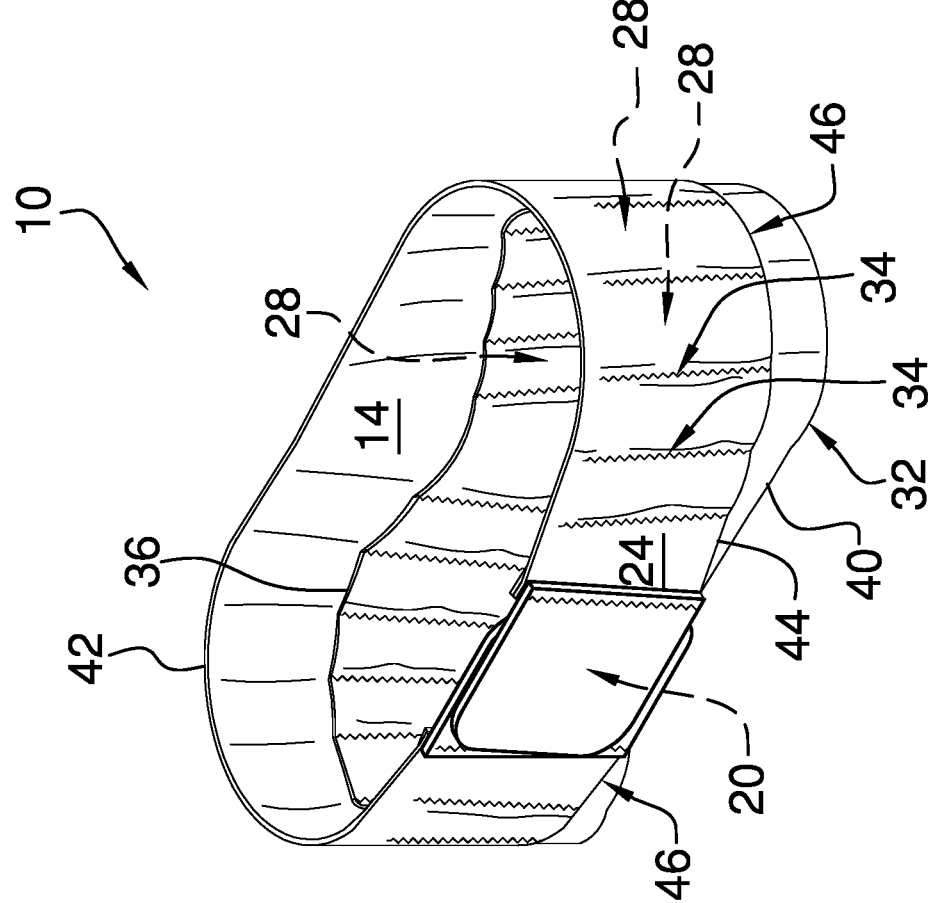
FIG. 2 is an isometric perspective view of an embodiment of the disclosure.
Figure 3:
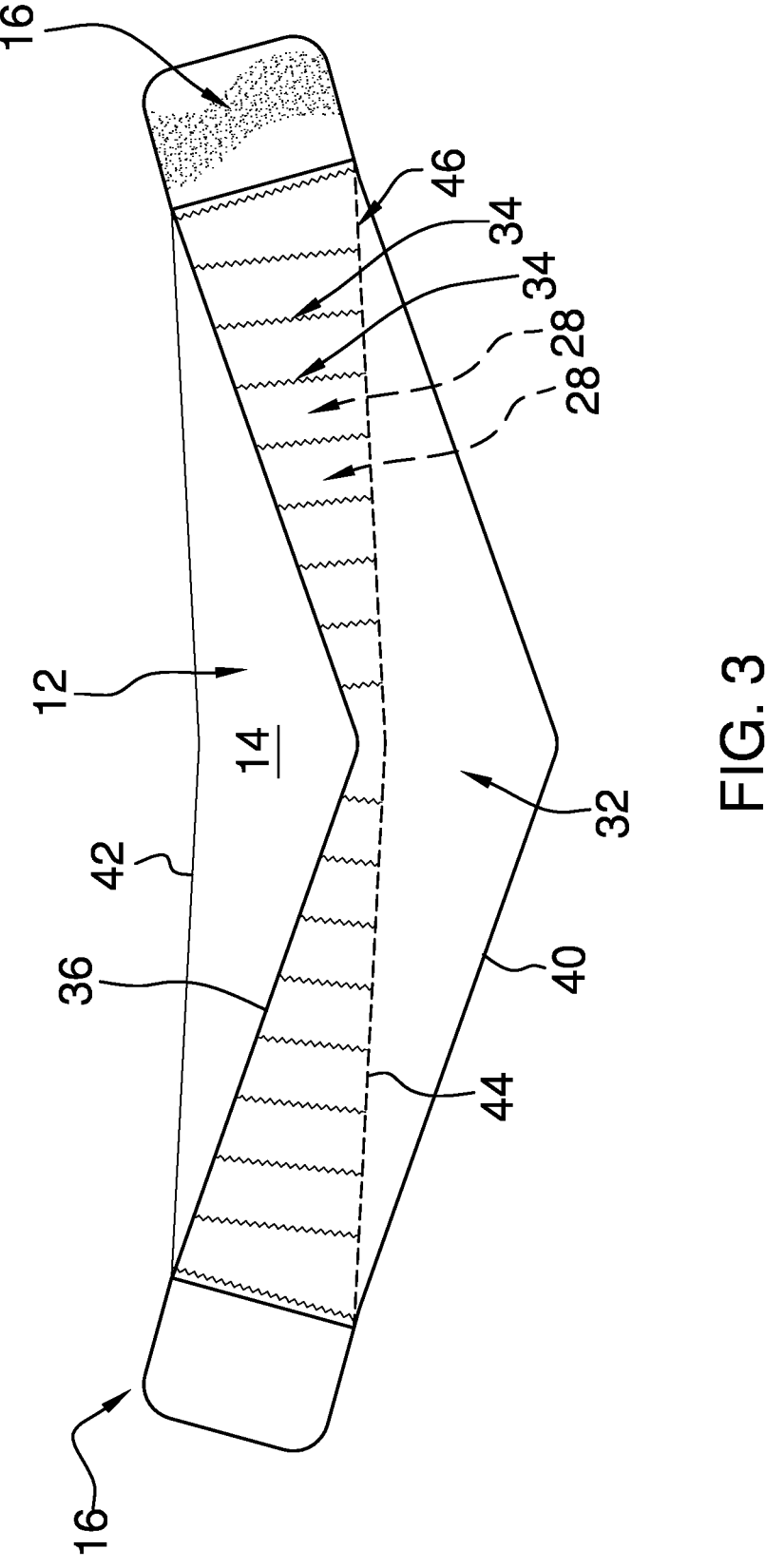
FIG. 3 is a front view of an embodiment of the disclosure.
Figure 4:
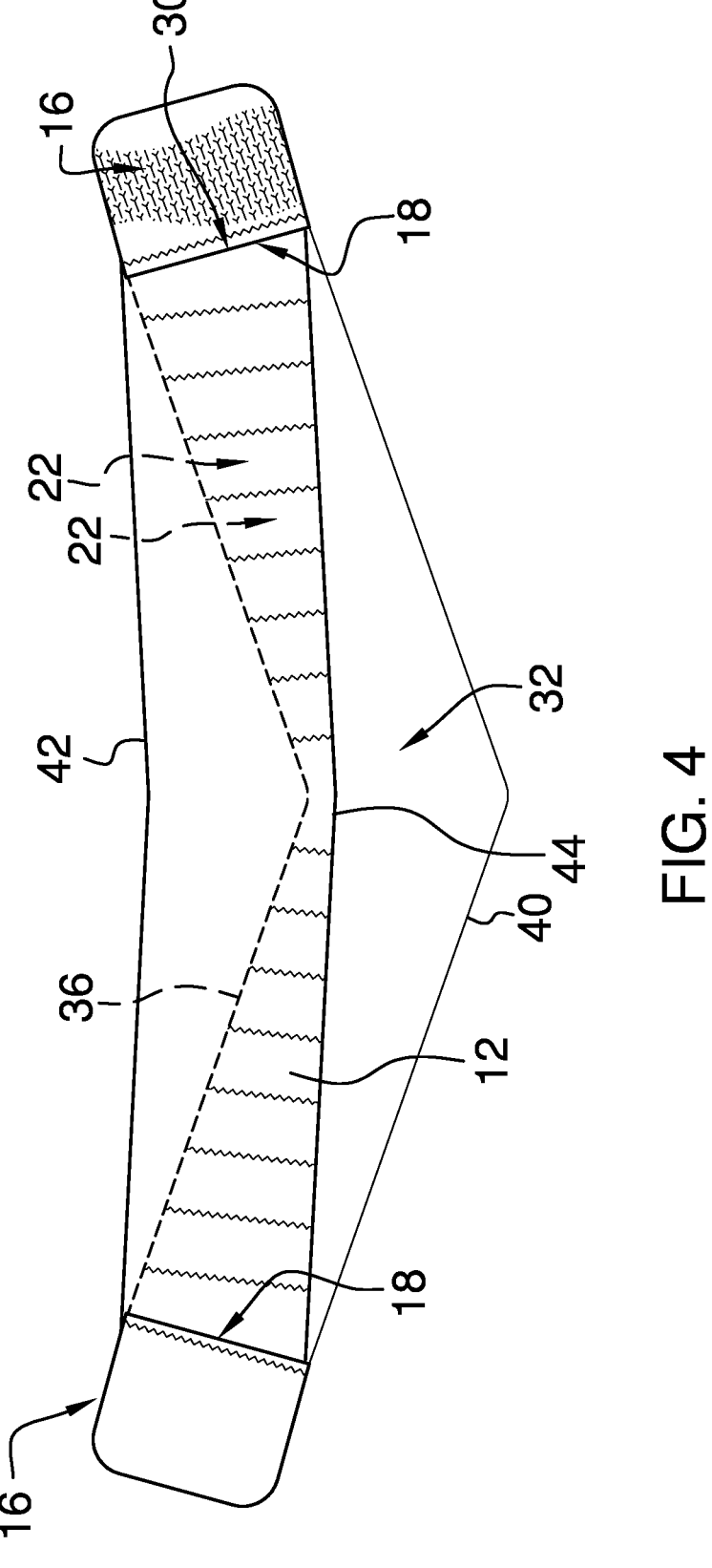
FIG. 4 is a rear view of an embodiment of the disclosure.
Figures 5, 6:
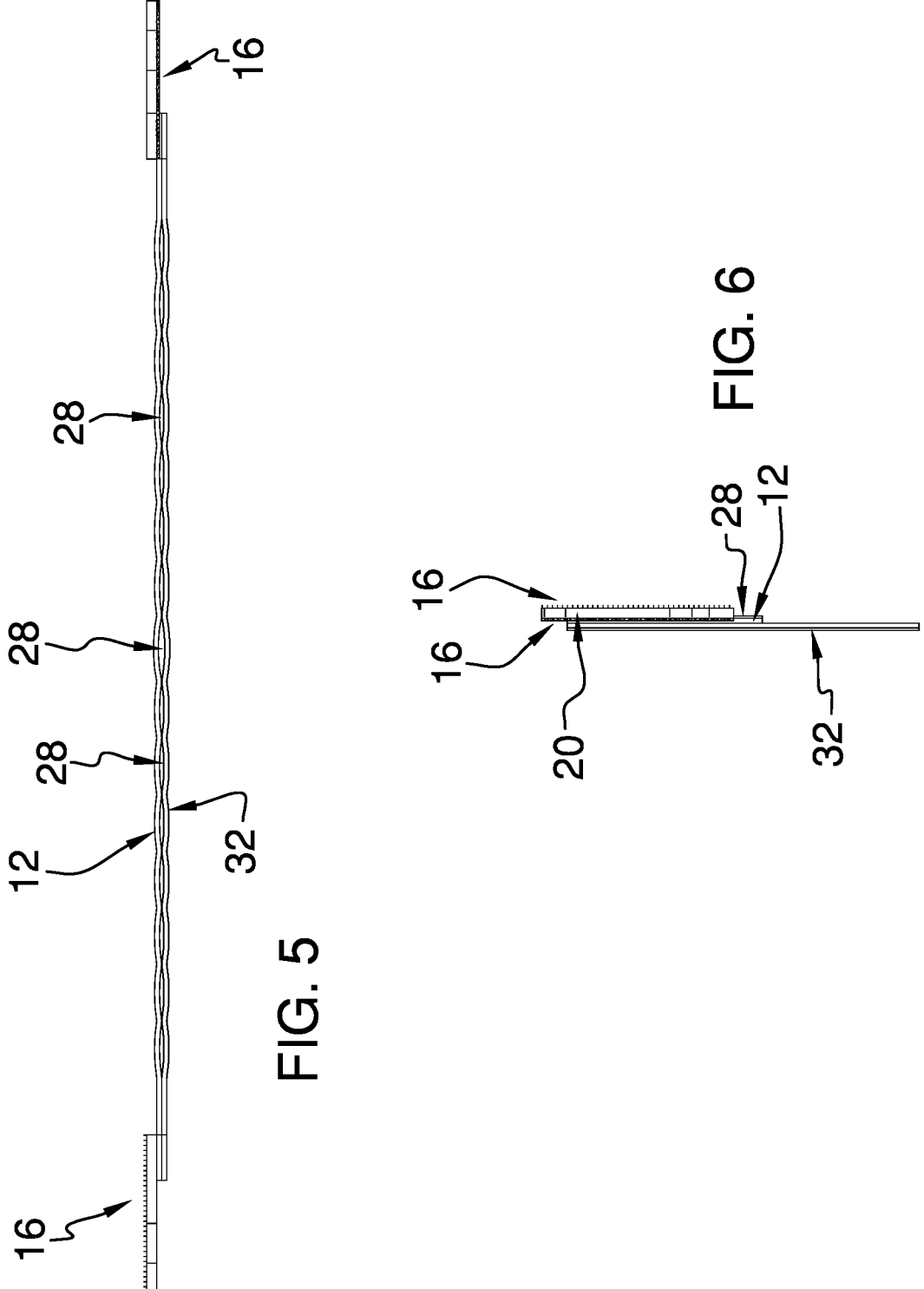
FIG. 5 is a top view of an embodiment of the disclosure.
FIG. 6 is an end view of an embodiment of the disclosure.
Figure 7:
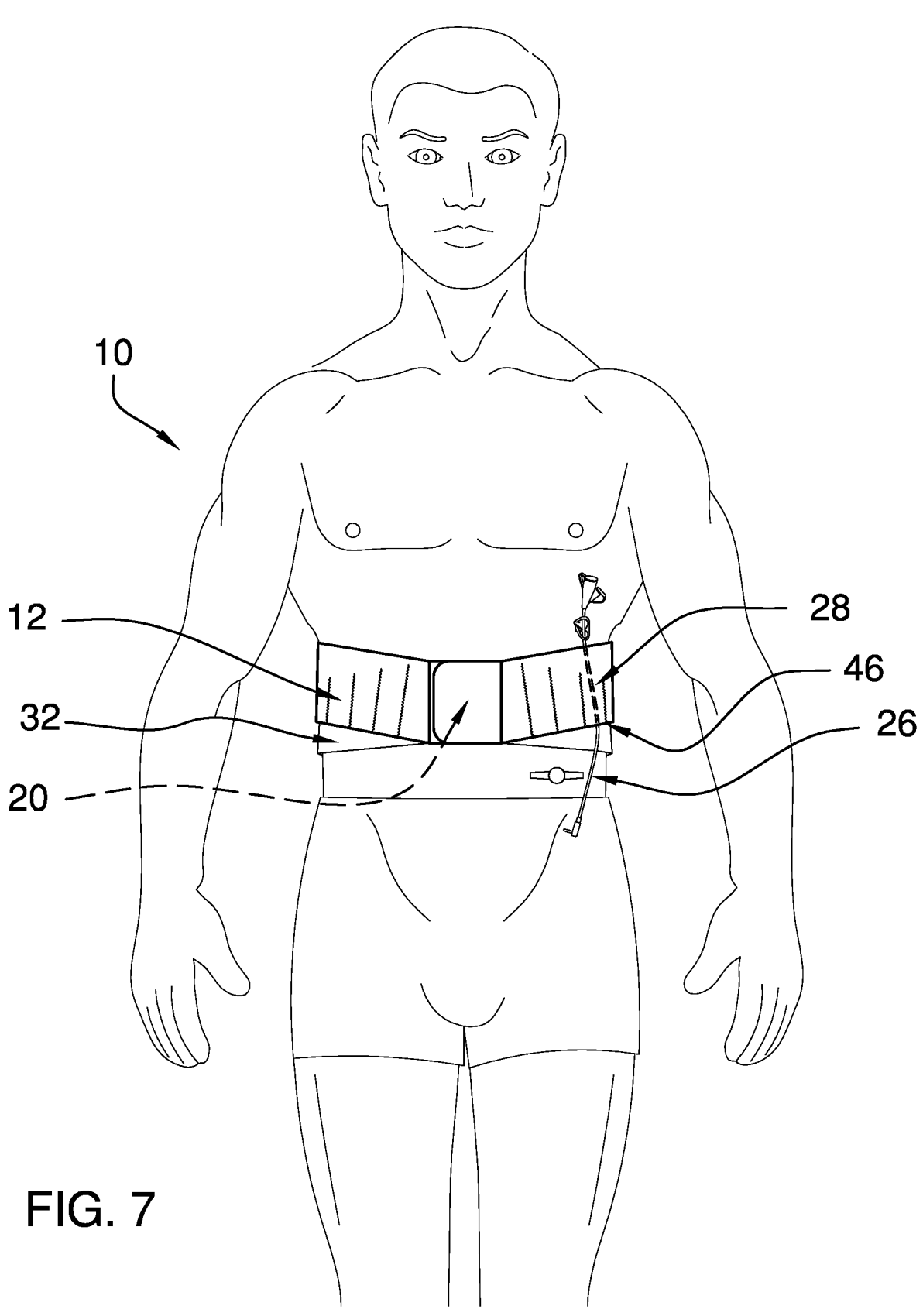
FIG. 7 is an in-use view of an embodiment of the disclosure.
Figure 8:
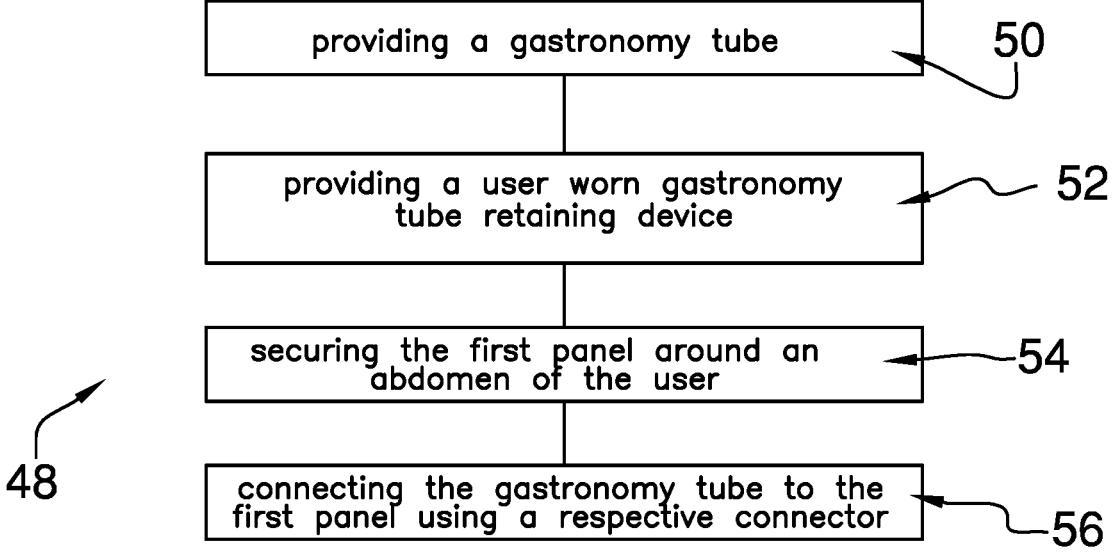
FIG. 8 is a flow diagram for a method utilizing an embodiment of the disclosure.

As best illustrated in FIGS. 1 through 8, the user worn gastronomy tube retaining device 10 generally comprises a first panel 12, which is resiliently flexible and which is configured to be removably secured around an abdomen of a user so that the first panel 12 encircles the abdomen with an inner surface 14 of the first panel 12 in contact with the abdomen, as shown in FIG. 7. The fasteners 16 of a pair of fasteners 16 are attached singly proximate to opposed ends 18 of the first panel 12. The fasteners 16 are selectively mutually attachable to removably secure the first panel 12 around the abdomen of the user. The pair of fasteners 16 may comprise a hook and loop fastener 20, as shown in FIGS. 3 and 4, or other fastening means, such as, but not limited to, button closures, snap closures, or the like.

A plurality of connectors 22 is attached to an outer surface 24 of the first panel 12. Each connector 22 is configured to selectively connect to a gastronomy tube 26 so that the gastronomy tube 26 is attached to the first panel 12. The connector 22 thus is configured to retain the gastronomy tube 26 in a substantially static position relative to the abdomen and to resist a pulling force applied to the gastronomy tube 26. As is shown in FIG. 2, the plurality of connectors 22 extends substantially between the opposed ends 18 of the first panel 12, thereby allowing the gastronomy tube 26 to be secured at various locations along the first panel 12. Such flexibility in attachment of the gastronomy tube 26 allows its attachment substantially independent of positioning of the user, who may be prone, supine, or lying on their side.

The present invention is anticipated to be useful in providing a comfortable means of retaining a gastronomy tube 26 in a desire position and limiting adverse complications induced by pulling on the gastronomy tube 26. Additionally, the present invention is anticipated to be useful in retaining other types of medical tubes in place, such as chest tubes or the like.

As shown in FIGS. 1-4, the plurality of connectors 22 comprises a plurality of sleeves 28, although the present invention anticipates the connectors 22 comprising other connecting means, such as, but not limited to, hook and loop straps, clips, or the like. Each sleeve 28 is substantially perpendicular to a longitudinal axis 30 of the first panel 12, which extends between the opposed ends 18 of the first panel 12.

As shown in FIGS. 1-4, the plurality of sleeves 28 is defined by a second panel 32 and a plurality of seams 34. Each seam 34 extends between the second panel 32 and the first panel 12 so that the second panel 32 is attached to the inner surface 14 of the first panel 12. Adjacently positioned seams 34 define a respective sleeve 28. The second panel 32 and the first panel 12 comprise one or both of polyether-polyurea copolymer and cotton so that the second panel 32 and the first panel 12 are resiliently stretchable and breathable. Thus, insertion of the gastronomy tube 26 into a respective sleeve 28 frictionally attaches it to the first panel 12.

As shown in FIG. 4, the first panel 12 is substantially elongated rectangularly shaped. The second panel 32 has an upper edge 36 and a lower edge 40, which are substantially parallel. The second panel 32 is flattened V-shaped so that its upper edge 36 and lower edge 40 are below a top edge 42 and a bottom edge 44 of the first panel 12, respectively. As such, each sleeve 28 has a lower opening 46 along the lower edge 40 of the second panel 32 that is accessible for insertion of the gastronomy tube 26.

While the configuration of the above paragraph is advantageous in that it provides an easily accessible lower opening 46 for each sleeve 28, other configurations also are anticipated by the present invention. For example, the second panel 32 also may be substantially elongated rectangularly shaped, with its upper edge 36 and lower edge 40 still being positioned below the top edge 42 and the bottom edge 44 of the first panel 12, respectively, wherein each sleeve 28 still would have an easily accessible lower opening 46.

In use, the user worn gastronomy tube 26 retaining device 10 enables a method of securing a gastronomy tube to a user 48. The method 48 comprises a first provision step 50, which entails providing a gastronomy tube 26. A second provision step 52 of the method 48 is providing a user worn gastronomy tube retaining device 10, according to the specification above. A first operational step 54 of the method 48 is securing the first panel 12 around an abdomen of the user. The first operational step 54 may comprise positioning the first panel 12 around the abdomen of the user and fastening a hook and loop fastener 20. A second operational step 56 of the method 48 is connecting the gastronomy tube 26 to the first panel 12 using a respective connector 22. The second operational step 56 may comprise insertion of the gastronomy tube 26 into a lower opening 46 of a respective sleeve 28 and through the respective sleeve 28.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A user worn gastronomy tube retaining device comprising:

a first panel configured to be removably secured around an abdomen of a user, such that the first panel encircles the abdomen with an inner surface of the first panel in contact with the abdomen, the first panel being resiliently flexible; and a plurality of connectors attached to an outer surface of the first panel, each connector of the plurality of connectors being configured for selectively connecting to a gastronomy tube, such that the gastronomy tube is attached to the first panel, wherein each connector of the plurality of connectors is configured for retaining the gastronomy tube in a substantially static position relative to the abdomen and for resisting a pulling force applied to the gastronomy tube;

wherein the plurality of connectors comprising a plurality of sleeves, each sleeve of the plurality of sleeves being substantially perpendicular to a longitudinal axis of the first panel extending between opposed ends of the first panel;

wherein the plurality of sleeves is defined by a second panel and a plurality of seams, each seam of the plurality of seams extending between the second panel and the first panel, such that the second panel is attached to the inner surface of the first panel, wherein adjacently positioned seams of the plurality of seams define a respective sleeve of the plurality of sleeves;

wherein the first panel are substantially elongated rectangularly shaped; and wherein the second panel having an upper edge and a lower edge, the upper edge and the lower edge being substantially parallel, the second panel being flattened V-shaped, such that the upper edge and the lower edge are below a top edge and a bottom edge of the first panel, respectively, and such that each sleeve of the plurality of sleeves has a lower opening along the lower edge of the second panel accessible for insertion of the gastronomy tube.

2. The user worn gastronomy tube retaining device of claim 1, further including a pair of fasteners attached singly proximate to opposed ends of the first panel, the fasteners of the pair of fasteners being selectively mutually attachable for removably securing the first panel around the abdomen of the user.

3. The user worn gastronomy tube retaining device of claim 2, wherein the pair of fasteners comprise a hook and loop fastener.

4. The user worn gastronomy tube retaining device of claim 1, wherein the plurality of connectors extends substantially between opposed ends of the first panel.

5. The user worn gastronomy tube retaining device of claim 1, wherein the second panel and the first panel comprising one or both of polyether-polyurea copolymer and cotton, such that the second panel and the first panel are resiliently stretchable and breathable.

6. A user worn gastronomy tube retaining device comprising:

a first panel configured to be removably secured around an abdomen of a user, such that the first panel encircles the abdomen with an inner surface of the first panel in contact with the abdomen, the first panel being resiliently flexible;

a pair of fasteners attached singly proximate to opposed ends of the first panel, the fasteners of the pair of fasteners being selectively mutually attachable for removably securing the first panel around the abdomen of the user, the pair of fasteners comprising a hook and loop fastener;

a plurality of connectors attached to an outer surface of the first panel, each connector of the plurality of connectors being configured for selectively connecting to a gastronomy tube, such that the gastronomy tube is attached to the first panel, wherein each connector of the plurality of connectors is configured for retaining the gastronomy tube in a substantially static position relative to the abdomen and for resisting a pulling force applied to the gastronomy tube, the plurality of connectors extending substantially between the opposed ends of the first panel, the plurality of connectors comprising a plurality of sleeves, each sleeve of the plurality of sleeves being substantially perpendicular to a longitudinal axis of the first panel extending between the opposed ends, the plurality of sleeves being defined by a second panel and a plurality of seams, each seam of the plurality of seams extending between the second panel and the first panel, such that the second panel is attached to the inner surface of the first panel, wherein adjacently positioned seams of the plurality of seams define a respective sleeve of the plurality of sleeves, the second panel and the first panel comprising one or both of polyether-polyurea copolymer and cotton, such that the second panel and the first panel are resiliently stretchable and breathable;

the first panel being substantially elongated rectangularly shaped; and the second panel having an upper edge and a lower edge, the upper edge and the lower edge being substantially parallel, the second panel being flattened V-shaped, such that the upper edge and the lower edge are below a top edge and a bottom edge of the first panel, respectively, and such that each sleeve of the plurality of sleeves has a lower opening along the lower edge of the second panel accessible for insertion of the gastronomy tube.

7. A method of securing a gastronomy tube to a user comprising the steps of:

providing a gastronomy tube;

providing a user worn gastronomy tube retaining device comprising:

a first panel configured to be removably secured around an abdomen of a user, such that the first panel encircles the abdomen with an inner surface of the first panel in contact with the abdomen, the first panel being resiliently flexible, and a plurality of connectors attached to an outer surface of the first panel, each connector of the plurality of connectors being configured for selectively connecting to a gastronomy tube, such that the gastronomy tube is attached to the first panel, wherein each connector of the plurality of connectors is configured for retaining the gastronomy tube in a substantially static position relative to the abdomen and for resisting a pulling force applied to the gastronomy tube;

securing the first panel around the abdomen of the user;

connecting the gastronomy tube to the first panel using a respective connector of the plurality of connectors;

the plurality of connectors comprising a plurality of sleeves, each sleeve of the plurality of sleeves being substantially perpendicular to a longitudinal axis of the first panel extending between the opposed ends, the plurality of sleeves being defined by a second panel and a plurality of seams, each seam of the plurality of seams extending between the second panel and the first panel, such that the second panel is attached to the inner surface of the first panel, wherein adjacently positioned seams of the plurality of seams define a respective sleeve of the plurality of sleeves, the second panel and the first panel comprising one or both of polyether-polyurea copolymer and cotton, such that the second panel and the first panel are resiliently stretchable and breathable;

the first panel being substantially elongated rectangularly shaped;

the second panel having an upper edge and a lower edge, the upper edge and the lower edge being substantially parallel, the second panel being flattened V-shaped, such that the upper edge and the lower edge are below a top edge and a bottom edge of the first panel, respectively, and such that each sleeve of the plurality of sleeves has a lower opening along the lower edge of the second panel accessible for insertion of the gastronomy tube; and the step of connecting the gastronomy tube to the first panel comprising insertion of the gastronomy tube into a lower opening of a respective sleeve and through the respective sleeve.

8. The method of claim 7, further including:

a pair of fasteners attached singly proximate to opposed ends of the first panel, the fasteners of the pair of fasteners being selectively mutually attachable for removably securing the first panel around the abdomen of the user, the pair of fasteners comprise a hook and loop fastener; and the step of securing the first panel around the abdomen of the user comprising positioning the first panel around the abdomen of the user and fastening the hook and loop fastener.

\* \* \* \* \*